United States Patent
Fikrig et al.

(10) Patent No.: US 11,452,769 B2
(45) Date of Patent: Sep. 27, 2022

(54) MOSQUITO SALIVA PROTEIN MALARIA VACCINE

(71) Applicant: Yale University, New Haven, CT (US)

(72) Inventors: Erol Fikrig, Guilford, CT (US); Yang Zhao, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 15/546,747

(22) PCT Filed: Jan. 26, 2016

(86) PCT No.: PCT/US2016/014839
§ 371 (c)(1),
(2) Date: Jul. 27, 2017

(87) PCT Pub. No.: WO2016/126457
PCT Pub. Date: Aug. 11, 2016

(65) Prior Publication Data
US 2018/0000911 A1    Jan. 4, 2018

Related U.S. Application Data

(60) Provisional application No. 62/110,756, filed on Feb. 2, 2015.

(51) Int. Cl.
| *A61K 39/015* | (2006.01) |
| *A61K 8/99* | (2017.01) |
| *A61K 35/68* | (2006.01) |
| *C07K 14/445* | (2006.01) |
| *C07K 16/20* | (2006.01) |
| *A61K 39/00* | (2006.01) |

(52) U.S. Cl.
CPC ............ *A61K 39/015* (2013.01); *A61K 8/99* (2013.01); *A61K 35/68* (2013.01); *C07K 14/445* (2013.01); *C07K 16/205* (2013.01); *A61K 2039/505* (2013.01); *Y10S 530/822* (2013.01)

(58) Field of Classification Search
CPC .. A61K 38/00; A61K 2039/53; A61K 39/005; A61K 2039/505; A61K 39/0003; A61K 39/015; A61K 2039/0003; C07K 14/43577; C07K 14/435; C07K 14/43563; C07K 16/18; Y10S 530/806; Y10S 530/855; Y10S 530/858; Y02A 50/412
See application file for complete search history.

(56) References Cited

U.S. PATENT DOCUMENTS

| 5,270,037 | A | 12/1993 | Bienzle | |
| 2003/0119733 | A1* | 6/2003 | Cerami | ............... C07K 14/445 435/5 |
| 2010/0297187 | A1* | 11/2010 | Stoloff | .................... A61P 33/14 530/324 |
| 2013/0022612 | A1* | 1/2013 | Sinnis | .................... A61P 33/06 530/389.1 |
| 2014/0206016 | A1* | 7/2014 | Lozano | .................... C12Q 1/04 435/7.1 |
| 2015/0313980 | A1* | 11/2015 | Janse | .................. A61K 39/015 435/258.2 |

FOREIGN PATENT DOCUMENTS

| EP | 2567706 | 3/2013 |
| WO | WO 2009034041 A2 * | 3/2009 |

OTHER PUBLICATIONS

Greenspan et al. Nature Biotechnology 17: 936-937, 1999.*
Rudinger J. In: Peptide Hormones. (Ed) JA Parsons, University Park Press, pp. 1-7, 1976.*
Skolnick et al. Trends in Biotechnology, 18: 34-39, 2000.*
Yoshida et al. Science 207: 71-73, 1980).*
Wang et al., 'Anopheles gambiae Circumsporozoite Protein-Binding Protein Facilitates Plasmodium Infection of Mosquito Salivary Glands,' The Journal of Infectious Diseases, 2013; 208:1161-9.

* cited by examiner

*Primary Examiner* — Sarvamangala Devi
(74) *Attorney, Agent, or Firm* — Riverside Law LLP

(57) ABSTRACT

The invention provides compositions and methods for preventing and treating infection by *Plasmodium* sporozoites.

4 Claims, 10 Drawing Sheets

Hit that appeared three times
AGAP000607-PA [Anopheles gambiae str. PEST] SG1L3
Hits that appeared twice
AGAP001374-PA TRIO protein
AGAP009257-PA
AGAP009918-PA
AGAP010750-PA
Hits that appeared once
AGAP001424-PA
AGAP001566-PA
AGAP007347-PA
AGAP007374-PA
AGAP008227-PA
AGAP008279-PA
AGAP008283-PA
AGAP011017-PA
AGAP011976-PA
AGAP012081-PA
AGAP013499-PA
AGAP002998-PA
AGAP003937-PA
AGAP004605-PA
AGAP011107-PA
AGAP013013-PA
AGAP009974-PA
AGAP000548-PA
AGAP011026-PA

Figure 6

MOSQUITO SALIVA PROTEIN MALARIA VACCINE

CROSS-REFERENCE TO RELATED APPLICATIONS

This application is the U.S. National Stage Application filed under 35 U.S.C. § 371 of International Patent Application No. PCT/US2016/014839, filed Jan. 26, 2016, which is entitled to priority under 35 U.S.C. § 119(e) to U.S. Provisional Patent Application No. 62/110,756, filed on Feb. 2, 2015, the contents of which are incorporated by reference herein in its entirety.

BACKGROUND OF THE INVENTION

Malaria is a mosquito-borne infectious disease caused by a eukaryotic protest of the genus *Plasmodium*. It is widespread in tropical and subtropical regions, including parts of the Americas, Asia, and Africa. Each year, there are more than 250 million cases of malaria, killing between one and three million people, the majority of whom are young children in sub-Saharan Africa. Despite efforts to reduce transmission and to increase treatment, there has been little change in which areas are at risk of this disease since 1992. Indeed, if the prevalence of malaria stays on its present course, the death rate could double in the next twenty years. Precise statistics are unknown because many cases occur in rural areas where people do not have access to hospitals or the means to afford healthcare. As a consequence, the majority of cases are undocumented.

Five species of the *Plasmodium* parasite can infect humans. The most serious forms of the disease are caused by *Plasmodium falciparum*, a protozoan parasite. It is transmitted by the female *Anopheles* mosquito. *P. falciparum* has the highest rate of complications and mortality; as of 2006, it has accounted for 91% of all 247 million human malarial infections (98% in Africa) and 90% of the deaths.

A wide variety of antimalarial drugs are available to treat malaria. Treatment of *P. falciparum* infections in endemic countries have recently been transformed by the use of combinations of drugs containing an artemisinin derivative. Severe malaria is treated with intravenous or intramuscular quinine, or increasingly, the artimisinin derivative artesunate. Several drugs are also available to prevent malaria in travelers to malaria-endemic countries (prophylaxis). Resistance has developed to several antimalarial drugs, most notably chloroquine.

Vaccines for malaria are under development, with no completely effective vaccine yet available. The first promising studies demonstrating the potential for a malaria vaccine were performed in 1967 by immunizing mice with live, radiation-attenuated sporozoites, providing protection to about 60% of the mice upon subsequent injection with normal, viable sporozoites. Since the 1970s, there has been a considerable effort to develop similar vaccination strategies within humans. However, the most advanced malaria vaccine candidates confer only partial protection against the clinical disease.

There is a need in the art for an effective malaria vaccine to treat or prevent *Plasmodium* sporozoite infection in patients. The present invention addresses this unmet need.

SUMMARY OF THE INVENTION

The present invention provides compositions and methods to prevent and treat infection by a *Plasmodium* sporozoite, i.e., malaria.

In one aspect, the invention relates to a vaccine comprising at least one mosquito salivary protein associated with a *Plasmodium* sporozoite.

In another aspect, the invention relates to a vaccine comprising at least one polypeptide selected from the group consisting of: AGAP000607-PA, or a AGAP000607-PA variant; AGAP001374-PA, or a AGAP001374-PA variant; AGAP009257-PA, or a AGAP009257-PA variant; AGAP009918-PA, or a AGAP009918-PA variant; AGAP010750-PA, or a AGAP010750-PA variant; AGAP001424-PA, or a AGAP001424-PA variant; AGAP001566-PA, or a AGAP001566-PA variant; AGAP007347-PA, or a AGAP007347-PA variant; AGAP008227-PA, or a AGAP008227-PA variant; AGAP008279-PA, or a AGAP008279-PA variant; AGAP008283-PA, or a AGAP008283-PA variant; AGAP011017-PA, or a AGAP011017-PA variant; AGAP011976-PA, or a AGAP011976-PA variant; AGAP012081-PA, or a AGAP012081-PA variant; AGAP013499-PA, or a AGAP013499-PA variant; AGAP002998-PA, or a AGAP002998-PA variant; AGAP003937-PA, or a AGAP003937-PA variant; AGAP004605-PA, or a AGAP004605-PA variant; AGAP011107-PA, or a AGAP011107-PA variant; AGAP013013-PA, or a AGAP013013-PA variant; AGAP009974-PA, or a AGAP009974-PA variant; AGAP000528-PA, or a AGAP000528-PA variant; and AGAP011026-PA, or a AGAP011026-PA variant.

In another aspect, the invention relates to a method of inducing an immune response in a subject against a *Plasmodium* sporozoite, the method comprising administering to the subject at least one of the vaccines of the present invention. In one embodiment, the subject is currently infected with *Plasmodium* sporozoites and the vaccine induces an immune response against *Plasmodium* sporozoites. In one embodiment, the subject is not currently infected with *Plasmodium* sporozoites and the vaccine induces an immune response against *Plasmodium* sporozoites.

In another aspect, the invention relates to a method of treating a subject infected with *Plasmodium* sporozoites, the method comprising administering to the subject at least one of the vaccines of the present invention. In one embodiment, the method further comprises the administration of an antibiotic.

In another aspect, the invention relates to a method of treating a subject infected with *Plasmodium* sporozoites, the method comprising administering to the subject at least one antibody, wherein the at least one antibody specifically binds to at least one of the polypeptides of the present invention. In one embodiment, the method further comprises the administration of an antibiotic.

In another aspect, the invention relates to an inhibitor composition useful for treating, reducing, or preventing *Plasmodium* sporozoite infection, wherein the inhibitor composition inhibits the interaction between a mosquito salivary protein associated with a *Plasmodium* sporozoite and the *Plasmodium* sporozoite. In one embodiment, the inhibitor composition specifically binds to the mosquito salivary protein associated with a *Plasmodium* sporozoite. In one embodiment, the inhibitor composition specifically binds to the *Plasmodium* sporozoite. In one embodiment, the inhibitor composition is at least one selected from the group consisting of a chemical compound, a protein, a peptide, a peptidomemetic, an antibody, a ribozyme, a small molecule chemical compound, a glycan, and an antisense nucleic acid molecule.

In another aspect, the invention relates to a method of treating a subject infected with *Plasmodium* sporozoites, the method comprising administering to the subject at least one of the inhibitor compositions of the present invention. In one embodiment, the method further comprises the administration of an antibtiotic.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1A depicts the results of fluorescence-activated cell sorting (FACS) to isolate and purify GFP-expressing *Plasmodium berghei* sporozoites from *Anopheles gambiae* mosquito salivary glands. FIG. 1B depicts a Venn diagram showing the number of *A. gambiae* proteins identified in three separate experiments that could potentially be associated with a *Plasmodium* sporozoite, as well as the number of proteins that were common to each experiment. FIG. 1C depicts the results of staining sporozoites purified from mosquito salivary glands (SG) and midguts (MG) with rabbit antibody against SG1L3.

FIG. 2A and FIG. 2B depict SG1L3 mRNA and protein expression, respectfully, in different regions of *A. gambiae*. FIG. 2C and FIG. 2D depict SG1L3 mRNA and protein expression, respectfully, in *A. gambiae* salivary glands with and without the invasion of *Plasmodium* sporozoites.

FIG. 3A compares *Plasmodium* liver burden in mice with no treatment, with a known *Plasmodium* sporozoite transmission inhibitor (3D11 mAb against *P. berghei* CSP) treatment, with an SG1L3 antibody treatment, and with an SG1L3 antibody and 3D11 mAb combination treatment. FIG. 3B depicts the effect of SG1L3 antibodies on parasitemia in mice. FIG. 3C and FIG. 3D depict the effects of a SG1L3 mAb (2A10) on parasitemia and *Plasmodium* infection, respectively, in mice.

FIG. 4A shows that mice generate strong reactions to whole mosquito salivary gland extracts and barely a detectable reaction to SG1L3. FIG. 4B shows gel analysis of immunogens from mosquito saliva.

FIG. 6 is list of the *A. gambiae* proteins identified in three separate experiments that could potentially be associated with a *Plasmodium* sporozoite.

DETAILED DESCRIPTION

Figure 1C:
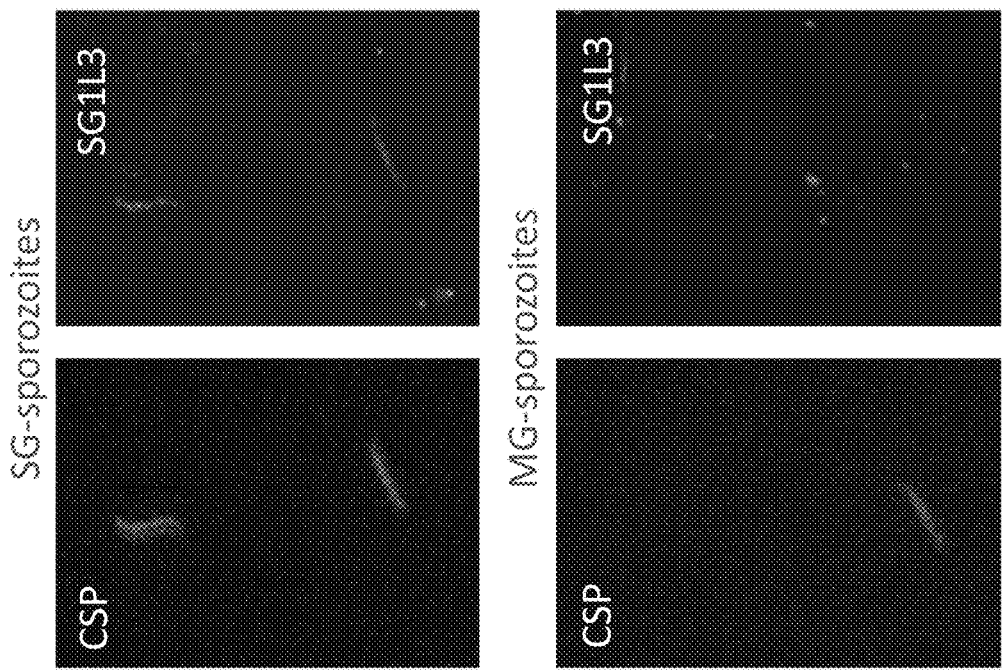
FIG. 1A through FIG. 1C depict the results of experiments performed to identify mosquito saliva proteins that are associated with a *Plasmodium* sporozoite.

The present invention provides compositions and methods to prevent and treat infection by a *Plasmodium* sporozoite, i.e., malaria. In one embodiment, the composition of the invention is a vaccine that induces the cell-mediated and/or humoral immunity directed against at least one mosquito salivary protein, or variants thereof, which is associated with a *Plasmodium* sporozoite. In various embodiments, the composition comprises at least one of the group consisting of AGAP000607-PA (a salivary gland-1 like 3 protein; hereinafter "SG1L3"), AGAP001374-PA (hereinafter "TRIO"), AGAP009257-PA, AGAP009918-PA, AGAP010750-PA, AGAP001424-PA, AGAP001566-PA, AGAP007347-PA, AGAP008227-PA, AGAP008279-PA, AGAP008283-PA, AGAP011017-PA, AGAP011976-PA, AGAP012081-PA, AGAP013499-PA, AGAP002998-PA, AGAP003937-PA, AGAP004605-PA, AGAP011107-PA, AGAP013013-PA, AGAP009974-PA, AGAP000528-PA, and AGAP011026-PA, or variants thereof. In a particular embodiment, the composition comprises SG1L3, or a variant thereof.

In another embodiment, the composition of the invention comprises at least one nucleic acid encoding a mosquito salivary protein, or variants thereof, associated with a *Plasmodium* sporozoite. In another embodiment, the composition of the invention comprises a nucleic acid sequence encoding SG1L3, or a variant thereof. In one embodiment, the composition comprises an antibody that specifically binds to SG1L3, or a variant thereof.

The invention provides methods of inducing an immune response for preventing or treating infection by a *Plasmodium* sporozoite. In one embodiment, the methods comprise administering at least one mosquito salivary protein, or variants thereof, associated with a *Plasmodium* sporozoite to a subject. In one embodiment, the methods comprise administering at least SG1L3, or a variant thereof, to a subject. In another embodiment, the methods comprise administering a nucleic acid encoding at least one mosquito salivary protein, or variants thereof, associated with a *Plasmodium* sporozoite to a subject. In another embodiment, the methods comprise administering a nucleic acid encoding at least SG1L3, or a variant thereof, to a subject.

The invention also includes inhibitor compositions and methods for inhibiting the interaction between the mosquito salivary protein associated with a *Plasmodium* sporozoite and the *Plasmodium* sporozoite.

The invention also provides methods of treating infection by a *Plasmodium* sporozoite in a subject in need thereof. In one embodiment, the method comprises administering to the subject at least one antibody that binds to a mosquito salivary protein, or variants thereof, associated with a *Plasmodium* sporozoite. In another embodiment, the method comprises administering to the subject at least one antibody that specifically binds to SG1L3, or a variant thereof.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section. It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "analog" or "functional analog" refers to a related modified form of a polypeptide, wherein at least one amino acid substitution, deletion, or addition has been made such that said analog retains substantially the same biological activity as the unmodified form, in vivo and/or in vitro.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample.

The term "agent" includes any substance, metabolite, molecule, element, compound, or a combination thereof. It includes, but is not limited to, e.g., protein, oligopeptide, small organic molecule, glycan, polysaccharide, polynucleotide, and the like. It can be a natural product, a synthetic compound, a chemical compound, or a combination of two or more substances. Unless otherwise specified, the terms "agent," "substance," and "compound" can be used interchangeably. Further, a "test agent" or "candidate agent" is generally a subject agent for use in an assay of the invention.

The term "binding" refers to a direct association between at least two molecules, due to, for example, covalent, electrostatic, hydrophobic, ionic and/or hydrogen-bond interactions.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the antigen binding region and would be understood to be so by a skilled person. See for example Chothia et al., (1989) Conformations of immunoglobulin hypervariable regions; Nature 342, p 877-883.

A "chimeric antibody" refers to a type of engineered antibody which contains a naturally-occurring variable region (light chain and heavy chains) derived from a donor antibody in association with light and heavy chain constant regions derived from an acceptor antibody.

"Contacting" refers to a process in which two or more molecules or two or more components of the same molecule or different molecules are brought into physical proximity such that they are able undergo an interaction. Molecules or components thereof may be contacted by combining two or more different components containing molecules, for example by mixing two or more solution components, preparing a solution comprising two or more molecules such as target, candidate or competitive binding reference molecules, and/or combining two or more flowing components.

As used herein, by "combination therapy" is meant that a first agent is administered in conjunction with another agent. "In conjunction with" refers to administration of one treatment modality in addition to another treatment modality. As such, "in conjunction with" refers to administration of one treatment modality before, during, or after delivery of the other treatment modality to the individual. Such combinations are considered to be part of a single treatment regimen or regime.

As used herein, the term "concurrent administration" means that the administration of the first therapy and that of a second therapy in a combination therapy overlap temporally with each other.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "donor antibody" refers to an antibody (monoclonal, and/or recombinant) which contributes the amino acid sequences of its variable regions, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody.

The term "acceptor antibody" refers to an antibody (monoclonal and/or recombinant) heterologous to the donor antibody, which contributes all (or any portion, but in some embodiments all) of the amino acid sequences encoding its heavy and/or light chain framework regions and/or its heavy and/or light chain constant regions to the first immunoglobulin partner. In certain embodiments a human antibody is the acceptor antibody.

An "effective amount" as used herein, means an amount which provides a therapeutic or prophylactic benefit.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

As used herein, the term "heavy chain antibody" or "heavy chain antibodies" comprises immunoglobulin molecules derived from camelid species, either by immunization with a peptide and subsequent isolation of sera, or by the cloning and expression of nucleic acid sequences encoding such antibodies. The term "heavy chain antibody" or "heavy chain antibodies" further encompasses immunoglobulin molecules isolated from an animal with heavy chain disease, or prepared by the cloning and expression of VH (variable heavy chain immunoglobulin) genes from an animal.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared multiplied by 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., 1989, Queen et al., Proc. Natl. Acad Sci USA, 86:10029-10032; 1991, Hodgson et al., Bio/Technology, 9:421). A suitable human acceptor antibody may be one selected from a conventional database, e.g., the KABAT database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanized antibodies (see for example EP-A-0239400 and EP-A-054951).

The term "immunoglobulin" or "Ig," as used herein, is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, the term "immune response" includes T-cell mediated and/or B-cell mediated immune responses. Exemplary immune responses include T cell responses, e.g., cytokine production and cellular cytotoxicity, and B cell responses, e.g., antibody production. In addition, the term immune response includes immune responses that are indirectly affected by T cell activation, e.g., antibody production (humoral responses) and activation of cytokine responsive cells, e.g., macrophages. Immune cells involved in the immune response include lymphocytes, such as B cells and T cells (CD4+, CD8+, Th1 and Th2 cells); antigen presenting cells (e.g., professional antigen presenting cells such as dendritic cells, macrophages, B lymphocytes, Langerhans cells, and non-professional antigen presenting cells such as keratinocytes, endothelial cells, astrocytes, fibroblasts, oligodendrocytes); natural killer cells; myeloid cells, such as macrophages, eosinophils, mast cells, basophils, and granulocytes.

As used herein, an "inhibitory-effective amount" is an amount that results in a detectable (e.g., measurable) amount of inhibition of an activity. In some instance, the activity is its ability to bind with another component.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "mutation," as used herein, refers to a change in nucleic acid or polypeptide sequence relative to a reference sequence (which is preferably a naturally-occurring normal or "wild-type" sequence), and includes translocations, deletions, insertions, and substitutions/point mutations. A "mutant" as used herein, refers to either a nucleic acid or protein comprising a mutation.

"Parenteral" administration of an immunogenic composition includes, e.g., subcutaneous (s.c.), intravenous (i.v.), intramuscular (i.m.), or intradermal (i.d.) injection, or infusion techniques.

The terms "patient," "subject," "individual," and the like are used interchangeably herein, and refer to any animal, or cells thereof, whether in vitro or in situ, amenable to the methods described herein. In certain non-limiting embodiments, the patient, subject or individual is a human.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "X," the presence of a molecule containing epitope X (or free, unlabeled A), in a reaction containing labeled "X" and the antibody, will reduce the amount of labeled X bound to the antibody.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "therapeutic" as used herein means a treatment and/or prophylaxis. A therapeutic effect is obtained by suppression, diminution, remission, or eradication of a disease state.

The term "therapeutically effective amount" refers to the amount of the subject compound that will elicit the biological or clinical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

"Variant" of the polypeptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the polypeptide is an alternative splice variant of the polypeptide of the present invention, (iv) fragments of the polypeptides and/or (v) one in which the polypeptide is fused with another polypeptide, such as a leader or secretory sequence or a sequence which is employed for purification (for example, His-tag) or for detection (for example, Sv5 epitope tag). The fragments include polypeptides generated via proteolytic cleavage (including multi-site proteolysis) of an original sequence. Variants may be post-translationally, or chemically modified. Such variants are deemed to be within the scope of those skilled in the art from the teaching herein.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The invention relates to the administration of at least one mosquito salivary protein associated with a *Plasmodium* sporozoite, to a subject to induce an immune response. Thus, the present invention provides a polypeptide or a combination of polypeptides, or a polynucleotide or a combination of polynucleotides, which are useful in inducing an immune response, for the treatment or prevention of infection by a *Plasmodium* sporozoite.

The invention provides an immunological composition comprising a polypeptide or combination of polypeptides derived from at least one mosquito salivary protein associated with a *Plasmodium* sporozoite, useful in eliciting an immune response. The compositions comprising one or more polypeptide of the invention not only are useful as a prophylactic therapeutic agent for immunoprotection, but are also useful as a therapeutic agent for treatment of an ongoing disease or disorder associated with infection by a *Plasmodium* sporozoite in a subject.

In one embodiment, the composition of the invention comprises a nucleic acid sequence encoding a mosquito salivary protein, or variants thereof, associated with a *Plasmodium* sporozoite. In various embodiments, the composition comprises at least one of the group consisting of AGAP000607-PA (a salivary gland-1 like 3 protein; hereinafter "SG1L3"), AGAP001374-PA (hereinafter "TRIO"), AGAP009257-PA, AGAP009918-PA, AGAP010750-PA, AGAP001424-PA, AGAP001566-PA, AGAP007347-PA, AGAP008227-PA, AGAP008279-PA, AGAP008283-PA, AGAP011017-PA, AGAP011976-PA, AGAP012081-PA, AGAP013499-PA, AGAP002998-PA, AGAP003937-PA, AGAP004605-PA, AGAP011107-PA, AGAP013013-PA, AGAP009974-PA, AGAP000528-PA, and AGAP011026-PA, or variants thereof. In a particular embodiment, the composition of the invention comprises a nucleic acid sequence encoding SG1L3, or a variant thereof. The skilled artisan will understand that the least one mosquito salivary protein associated with a *Plasmodium* sporozoite, useful in eliciting an immune response, can be used each alone or in any combination for eliciting an immune response.

The present invention also provides methods of preventing, inhibiting, and treating infection by a *Plasmodium* sporozoite in a subject in need thereof. In one embodiment, the methods of the invention induce immunity against Plasmodium sporozoites in the subject, by generating an immune response in the subject directed to at least one polypeptide, such as SG1L3. In one embodiment, the methods of the invention induce production of SG1L3-specific antibodies in the subject.

In one embodiment, the methods of the invention prevent Plasmodium sporozoite related disease or disorder in a subject in need thereof. In one embodiment, the methods of the invention comprise administering to the subject a composition comprising at least a portion of at least one mosquito salivary protein associated with a Plasmodium sporozoite to a subject. In another embodiment, the methods of the invention comprise administering to the subject a composition comprising a nucleic acid sequence encoding at least one mosquito salivary protein associated with a Plasmodium sporozoite to a subject.

The invention also includes inhibitor compositions and methods for inhibiting the interaction between the mosquito salivary protein associated with a Plasmodium sporozoite and the Plasmodium sporozoite.

Compositions

The present invention provides compositions, including polypeptides, nucleotides, vectors, and vaccines, that when administered to a subject, elicit an immune response directed against Plasmodium sporozoites, including an immune response directed against at least one mosquito salivary protein associated with a Plasmodium sporozoite. Further, when the compositions are administered to a subject, they elicit an immune response that serves to protect the subject against diseases or disorders associated with Plasmodium sporozoite infection.

In one embodiment, the present invention provides compositions that are useful as immunomodulatory agents, for example, in initiating or stimulating an immune response and in preventing or diminishing Plasmodium sporozoite related disease or disorder. In various embodiments, the immunomodulatory agents comprise at least one mosquito salivary protein associated with a Plasmodium sporozoite. In various embodiments, the immunomodulatory agents comprise at least one of the group consisting of AGAP000607-PA (a salivary gland-1 like 3 protein; hereinafter "SG1L3"), AGAP001374-PA (hereinafter "TRIO"), AGAP009257-PA, AGAP009918-PA, AGAP010750-PA, AGAP001424-PA, AGAP001566-PA, AGAP007347-PA, AGAP008227-PA, AGAP008279-PA, AGAP008283-PA, AGAP011017-PA, AGAP011976-PA, AGAP012081-PA, AGAP013499-PA, AGAP002998-PA, AGAP003937-PA, AGAP004605-PA, AGAP011107-PA, AGAP013013-PA, AGAP009974-PA, AGAP000528-PA, and AGAP011026-PA, or variants thereof. In one embodiment, the immune response is not detrimental to the host and therefore the compositions of the invention are useful as a vaccine, to prevent or to diminish the likelihood of a subject becoming infected. In one embodiment, the immunomodulatory agents are administered in combination with an adjuvant. In another embodiment, the immunomodulatory agents are administered in the absence of an adjuvant.

Mosquito salivary proteins associated with a Plasmodium sporozoite can be used as immunostimulatory agents to induce the production of antibodies to protect, prevent, or reduce the likelihood of developing a Plasmodium sporozoite induced disease or disorder. In one embodiment, the composition of the invention comprises a SG1L3 polypeptide, or a variant thereof. The skilled artisan will understand that the least one mosquito salivary protein associated with a Plasmodium sporozoite, useful in eliciting an immune response, can each be used alone or in any combination for eliciting an immune response.

The present invention also provides polynucleotides that encode the polypeptides described herein. Therefore, in one embodiment, the composition of the invention comprises a nucleic acid sequence encoding SG1L3, or a variant thereof. The skilled artisan will understand that the least one mosquito salivary protein associated with a Plasmodium sporozoite, useful in eliciting an immune response, can each be used alone or in any combination for eliciting an immune response.

In various embodiments, the invention provides a polypeptide, or a fragment of a polypeptide, a homolog, a mutant, a variant, a derivative or a salt of a polypeptide as elsewhere described herein, wherein the immunogenic activity of the polypeptide or fragment thereof is retained.

The invention should also be construed to include any form of a polypeptide having substantial homology to the polypeptides disclosed herein. Preferably, a polypeptide which is "substantially homologous" is about 50% homologous, more preferably about 70% homologous, even more preferably about 80% homologous, more preferably about 90% homologous, even more preferably, about 95% homologous, and even more preferably about 99% homologous to amino acid sequence of the polypeptides disclosed herein.

In one embodiment, the polypeptide or combination of polypeptides of the present invention are capable of generating a specific immune response. In another embodiment, the polypeptide or combination of polypeptides of the present invention are capable of generating specific antibodies.

Polypeptides of the present invention can be prepared using well known techniques. For example, the polypeptides can be prepared synthetically, using either recombinant DNA technology or chemical synthesis. Polypeptides of the present invention may be synthesized individually or as longer polypeptides composed of two or more polypeptides. The polypeptides of the present invention can be isolated, i.e., substantially free of other naturally occurring host cell proteins and fragments thereof.

The polypeptides of the present invention may contain modifications, such as glycosylation, aglycosylation, side chain oxidation, or phosphorylation; so long as the modifications do not destroy the immunologic activity of the polypeptides. Other modifications include incorporation of D-amino acids or other amino acid mimetics that can be used, for example, to increase the serum half-life of the polypeptides.

The polypeptides of the invention can be modified whereby the amino acid is substituted for a different amino acid in which the properties of the amino acid side-chain are conserved (a process known as conservative amino acid substitution). Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). Note that the parenthetic letters indicate the one-letter codes of amino acids. As used herein, X stands for any amino acid.

The polypeptides of the invention can be prepared as a combination, which includes two or more of polypeptides of the invention, for use as a vaccine for the reduction, prevention, or treatment of *Plasmodium* sporozoite infection. The polypeptides may be in a cocktail or may be conjugated to each other using standard techniques. For example, the polypeptides can be expressed as a single polypeptide sequence. The polypeptides in the combination may be the same or different.

The present invention should also be construed to encompass "analogs," "mutants," "derivatives," and "variants" of the polypeptides of the invention (or of the DNA encoding the same) which analogs, mutants, derivatives and variants are polypeptides which are altered in one or more amino acids (or, when referring to the nucleotide sequence encoding the same, are altered in one or more base pairs) such that the resulting polypeptide (or DNA) is not identical to the sequences recited herein, but has the same biological property as the polypeptides disclosed herein.

The nucleic acid sequences include both the DNA sequence that is transcribed into RNA and the RNA sequence that is translated into a polypeptide. According to other embodiments, the polynucleotides of the invention are inferred from the amino acid sequence of the polypeptides of the invention. As is known in the art several alternative polynucleotides are possible due to redundant codons, while retaining the biological activity of the translated polypeptides.

Further, the invention encompasses an isolated nucleic acid encoding a polypeptide having substantial homology to the polypeptides disclosed herein. Preferably, the nucleotide sequence of an isolated nucleic acid encoding a polypeptide of the invention is "substantially homologous," that is, is about 60% homologous, more preferably about 70% homologous, even more preferably about 80% homologous, more preferably about 90% homologous, even more preferably, about 95% homologous, and even more preferably about 99% homologous to a nucleotide sequence of an isolated nucleic acid encoding a polypeptide of the invention.

It is to be understood explicitly that the scope of the present invention encompasses homologs, analogs, variants, fragments, derivatives and salts, including shorter and longer polypeptides and polynucleotides, as well as polypeptide and polynucleotide analogs with one or more amino acid or nucleic acid substitution, as well as amino acid or nucleic acid derivatives, non-natural amino or nucleic acids and synthetic amino or nucleic acids as are known in the art, with the stipulation that these modifications must preserve the immunologic activity of the original molecule. Specifically any active fragments of the active polypeptides as well as extensions, conjugates and mixtures are included and are disclosed herein according to the principles of the present invention.

The invention should be construed to include any and all isolated nucleic acids which are homologous to the nucleic acids described and referenced herein, provided these homologous nucleic acids encode polypeptides having the biological activity of the polypeptides disclosed herein.

The skilled artisan would understand that the nucleic acids of the invention encompass an RNA or a DNA sequence encoding a polypeptide of the invention, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Any and all combinations of modifications of the nucleotide sequences are contemplated in the present invention.

Further, any number of procedures may be used for the generation of mutant, derivative or variant forms of a protein of the invention using recombinant DNA methodology well known in the art such as, for example, that described in Sambrook et al. (2012, Molecular Cloning: A Laboratory Manual, Cold Spring Harbor Laboratory, New York), and in Ausubel et al. (1997, Current Protocols in Molecular Biology, John Wiley & Sons, New York). Procedures for the introduction of amino acid changes in a polypeptide or polypeptide by altering the DNA sequence encoding the polypeptide are well known in the art and are also described in these, and other, treatises.

Vectors

The nucleic acids encoding the polypeptide or combinations of polypeptides of the invention of the invention can be incorporated into suitable vectors, including but not limited to, plasmids and retroviral vectors. Such vectors are well known in the art and are therefore not described in detail herein.

In one embodiment, the invention includes a nucleic acid sequence encoding one or more polypeptides of the invention operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (2012, Molecular Cloning: A Laboratory Manual, Cold Spring Harbor Laboratory, New York), and in Ausubel et al. (1997, Current Protocols in Molecular Biology, John Wiley & Sons, New York). The incorporation of a desired polynucleotide into a vector and the choice of vectors is well-known in the art as described in, for example, Sambrook et al. (2012), and in Ausubel et al. (1997).

The polynucleotide can be cloned into a number of types of vectors. However, the present invention should not be construed to be limited to any particular vector. Instead, the present invention should be construed to encompass a wide plethora of vectors which are readily available and/or well-known in the art. For example, the polynucleotide of the invention can be cloned into a vector including, but not limited to a plasmid, a phagemid, a phage derivative, an animal virus, and a cosmid. Vectors of particular interest include expression vectors, replication vectors, probe generation vectors, and sequencing vectors.

In specific embodiments, the expression vector is selected from the group consisting of a viral vector, a bacterial vector and a mammalian cell vector. Numerous expression vector systems exist that comprise at least a part or all of the compositions discussed above. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector. Viral vector technology is well known in the art and is described, for example, in Sambrook et al. (2012), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193).

For expression of the desired nucleotide sequences of the invention, at least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 genes, a discrete element overlying the start site itself helps to fix the place of initiation.

Additional promoter elements, i.e., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR, in connection with the compositions disclosed herein (U.S. Pat. Nos. 4,683,202, 5,928, 906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (2012). The promoters employed may be constitutive, tissue-specific, inducible, and/or useful under the appropriate conditions to direct high level expression of the introduced DNA segment, such as is advantageous in the large-scale production of recombinant proteins and/or polypeptides. The promoter may be heterologous or endogenous.

One example of a constitutive promoter sequence is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, the invention includes the use of a tissue-specific promoter, where the promoter is active only in a desired tissue. Tissue-specific promoters are well known in the art and include, but are not limited to, the HER-2 promoter and the PSA associated promoter sequences.

In order to assess the expression of the nucleotide sequences encoding the polypeptide or combinations of polypeptides of the invention, the expression vector to be introduced into a cell can also contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (see, e.g., Ui-Tei et al., 2000 FEBS Lett. 479:79-82). Suitable expression systems are well known and may be prepared using well known techniques or obtained commercially. Internal deletion constructs may be generated using unique internal restriction sites or by partial digestion of non-unique restriction sites. Constructs may then be transfected into cells that display high levels of siRNA polynucleotide and/or polypeptide expression. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In some embodiments, the expression vector is modified to increase the expression of the desired polypeptide. For example, the vector can undergo codon optimization to improve expression in a given mammal. For example, the vector can be codon-optimized for human expression. In another embodiment, the expression vector comprises an effective secretory leader. An exemplary leader is an IgE leader sequence. In another embodiment, the expression vector comprises a Kozak element to initiate translation. In another embodiment, the nucleic acid is removed of cis-acting sequence motifs/RNA secondary structures that would impede translation. Such modifications, and others, are known in the art for use in DNA vaccines (Kutzler et al, 2008, Nat. Rev. Gen. 9: 776-788; PCT App. No. PCT/US2007/000886; PCT App. No.; PCT/US2004/018962).

Vaccine

For an antigenic composition to be useful as a vaccine, the antigenic composition must induce an immune response to the antigen in a cell, tissue or subject (e.g., a human). In some embodiments, the vaccine induces a protective immune response in the subject. As used herein, an "immunological composition" may comprise, by way of examples, an antigen (e.g., a polypeptide), a nucleic acid encoding an antigen (e.g., an antigen expression vector), or a cell expressing or presenting an antigen. In particular embodiments the antigenic composition comprises or encodes all or part of any polypeptide antigen described herein, or an immunologically functional equivalent thereof. In other embodiments, the antigenic composition is in a mixture that comprises an additional immunostimulatory agent or nucleic acids encoding such an agent. Immunostimulatory agents include but are not limited to an additional antigen, an immunomodulator, an antigen presenting cell or an adjuvant. In other embodiments, one or more of the additional agent(s) is covalently bonded to the antigen or an immunostimulatory agent, in any combination. In certain embodiments, the antigenic composition is conjugated to or comprises an HLA anchor motif amino acids.

In the context of the present invention, the term "vaccine" (also referred to as an immunogenic composition) refers to a substance that induces anti-*Plasmodium* sporozoite immunity or suppresses *Plasmodium* sporozoites upon inoculation into an animal. In various embodiments, the vaccine of the invention comprises at least one mosquito salivary protein associated with a *Plasmodium* sporozoite that can be administered to a subject to induce an immune response. In various embodiments, the vaccine of the invention comprises at least one of the group consisting of AGAP000607-PA (a salivary gland-1 like 3 protein; hereinafter "SG1L3"), AGAP001374-PA (hereinafter "TRIO"), AGAP009257-PA, AGAP009918-PA, AGAP010750-PA, AGAP001424-PA, AGAP001566-PA, AGAP007347-PA, AGAP008227-PA, AGAP008279-PA, AGAP008283-PA, AGAP011017-PA, AGAP011976-PA, AGAP012081-PA, AGAP013499-PA, AGAP002998-PA, AGAP003937-PA, AGAP004605-PA, AGAP011107-PA, AGAP013013-PA, AGAP009974-PA, AGAP000528-PA, and AGAP011026-PA, or variants thereof. In one embodiment, the vaccine is administered in combination with an adjuvant. In another embodiment, the vaccine is administered in the absence of an adjuvant.

A vaccine of the present invention may vary in its composition of nucleic acid and/or cellular components. In a non-limiting example, a nucleic encoding an antigen might also be formulated with an adjuvant. Of course, it will be understood that various compositions described herein may further comprise additional components. For example, one or more vaccine components may be comprised in a lipid or liposome. In another non-limiting example, a vaccine may comprise one or more adjuvants. A vaccine of the present invention, and its various components, may be prepared and/or administered by any method disclosed herein or as would be known to one of ordinary skill in the art, in light of the present disclosure.

In one embodiment, the polypeptide vaccine of the invention includes, but is not limited to at least one polypeptide, or a fragment thereof, optionally mixed with adjuvant substances. In some embodiments, the polypeptide is introduced together with an antigen presenting cell (APC). The most common cells used for the latter type of vaccine are bone marrow and peripheral blood derived dendritic cells, as these cells express costimulatory molecules that help activation of T cells. WO00/06723 discloses a cellular vaccine composition which includes an APC presenting tumor associated antigen polypeptides. Presenting the polypeptide can be effected by loading the APC with a polynucleotide (e.g., DNA, RNA) encoding the polypeptide or loading the APC with the polypeptide itself.

Thus, the present invention also encompasses a method of inducing *Plasmodium* sporozoite immunity using one or more of polypeptides described herein. When a certain polypeptide or combination of polypeptides induces a *Plasmodium* sporozoite immune response after inoculation into an animal, the polypeptide or combination of polypeptides is understood to have an immunity inducing effect. The induction of *Plasmodium* sporozoite immunity by a polypeptide or combination of polypeptides can be detected by observing the response of the immune system, in vivo or in vitro, by the host against the polypeptide, or combination of polypeptides.

In another embodiment, the methods of the invention comprise administering to the subject a bacterium or virus comprising a nucleic acid sequence encoding at least one mosquito salivary protein associated with a *Plasmodium* sporozoite. In another embodiment, the methods of the invention comprise administering to the subject a bacterium or virus expressing at least a portion of at least one mosquito salivary protein associated with a *Plasmodium* sporozoite. In another embodiment, the methods of the invention comprise administering to the subject a bacterium or virus comprising at least a portion of at least one mosquito salivary protein associated with a *Plasmodium* sporozoite.

For example, a method for detecting the induction of cytotoxic T lymphocytes is well known. A foreign substance that enters the living body is presented to T cells and B cells by the action of APCs. T cells that respond to the antigen presented by APC in an antigen-specific manner differentiate into cytotoxic T cells (also referred to as cytotoxic T lymphocytes or CTLs) due to stimulation by the antigen. These antigen stimulated cells then proliferate. This process is referred to herein as "activation" of T cells. Therefore, CTL induction by a certain polypeptide or combination of polypeptides of the invention can be evaluated by presenting the polypeptide to a T cell by APC, and detecting the induction of CTL. Furthermore, APCs have the effect of activating CD4+ T cells, CD8+ T cells, macrophages, eosinophils and NK cells.

A method for evaluating the inducing action of CTL using dendritic cells (DCs) as APC is well known in the art. DC is a representative APC having the strongest CTL inducing action among APCs. In this method, the polypeptide or combination of polypeptides is initially contacted with DC and then this DC is contacted with T cells. Detection of T cells having cytotoxic effects against the cells of interest after the contact with DC shows that the polypeptide or combination of polypeptides has an activity of inducing the cytotoxic T cells. Furthermore, the induced immune response can be also examined by measuring IFN-gamma produced and released by CTL in the presence of antigen-presenting cells that carry immobilized polypeptide or combination of polypeptides by visualizing using anti-IFN-gamma antibodies, such as an ELISPOT assay.

Apart from DC, peripheral blood mononuclear cells (PBMCs) may also be used as the APC. The induction of CTL is reported to be enhanced by culturing PBMC in the presence of GM-CSF and IL-4. Similarly, CTL has been shown to be induced by culturing PBMC in the presence of keyhole limpet hemocyanin (KLH) and IL-7.

The polypeptide or combination of polypeptides, confirmed to possess CTL inducing activity by these methods, are polypeptides having DC activation effect and subsequent CTL inducing activity. Therefore, a polypeptide or combination of polypeptides that induce CTL against *Plasmodium* sporozoite A and *Plasmodium* sporozoite B are useful as vaccines against *Plasmodium* sporozoite associated disease or disorder. Furthermore, CTL that have acquired cytotoxicity due to presentation of the polypeptide or combination of polypeptides by APC can be also used as vaccines against *Plasmodium* sporozoite infection.

Generally, when using a polypeptide for cellular immunotherapy, efficiency of the CTL-induction can be increased by combining a plurality of polypeptides having different structures and contacting them with DC. Therefore, when stimulating DC with protein fragments, it is advantageous in certain embodiments to use a mixture of multiple types of fragments.

The induction of *Plasmodium* sporozoite immunity by a polypeptide or combination of polypeptides can be further confirmed by observing the induction of antibody production against the *Plasmodium* sporozoites. For example, when antibodies against a polypeptide or combination of polypeptides are induced in a laboratory animal immunized with the polypeptide or combination of polypeptides, and when *Plasmodium* sporozoite associated disease or disorder is suppressed by those antibodies, the polypeptide or combination of polypeptides are understood to induce anti-*Plasmodium* sporozoite immunity.

*Plasmodium* sporozoite immunity can be induced by administering a vaccine of the invention, and the induction of *Plasmodium* sporozoite immunity enables treatment and prevention of pathologies associated with *Plasmodium* sporozoite. Thus, the invention provides a method for treating or preventing infection by a *Plasmodium* sporozoite. The therapeutic compounds or compositions of the invention may be administered prophylactically or therapeutically to subjects suffering from, at risk of developing, or susceptible to developing, *Plasmodium* sporozoite infection. Such subjects may be identified using standard clinical methods. In the context of the present invention, prophylactic administration occurs prior to the manifestation of overt clinical symptoms of disease, such that a disease or disorder is prevented or alternatively delayed in its progression. In the context of the field of medicine, the term "prevent" encompasses any activity which reduces the burden of mortality or morbidity from disease. Prevention can occur at primary, secondary and tertiary prevention levels. While primary prevention avoids the development of a disease, secondary and tertiary levels of prevention encompass activities aimed at preventing the progression of a disease and the emergence of symptoms as well as reducing the negative impact of an already established disease by restoring function and reducing disease-related complications.

The polypeptide or combination of polypeptides of the invention having immunological activity, or a polynucleotide or vector encoding such a polypeptide or combination of polypeptides, may optionally be combined with an adjuvant. An adjuvant refers to a compound that enhances the immune response against the polypeptide or combination of polypeptides when administered together (or successively) with the polypeptide having immunological activity. Non-limiting examples of suitable adjuvants include cholera toxin, salmonella toxin, alum and such, but are not limited thereto. Furthermore, a vaccine of this invention may be combined appropriately with a pharmaceutically acceptable carrier. Examples of such carriers are sterilized water, physiological saline, phosphate buffer, culture fluid and such. Furthermore, the vaccine may contain as necessary, stabilizers, suspensions, preservatives, surfactants and such. The vaccine is administered systemically or locally. Vaccine administration may be performed by single administration or boosted by multiple administrations.

Administration

In one embodiment, the methods of the present invention comprise administering to a subject a composition comprising at least one polypeptide of the invention, and/or at least one polynucleotide encoding at least one polypeptide of the invention. Administration of the composition can comprise, for example, intramuscular, intravenous, peritoneal, subcutaneous, intradermal, as well as topical administration.

The actual dose and schedule can vary depending on whether the compositions are administered in combination with other pharmaceutical compositions, or depending on inter-individual differences in pharmacokinetics, drug disposition, and metabolism. Similarly, amounts can vary in in vitro applications depending on the particular cell line utilized (e.g., based on the number of vector receptors present on the cell surface, or the ability of the particular vector employed for gene transfer to replicate in that cell line). Furthermore, the amount of vector to be added per cell will likely vary with the length and stability of the therapeutic gene inserted in the vector, as well as also the nature of the sequence, and is particularly a parameter which needs to be determined empirically, and can be altered due to factors not inherent to the methods of the present invention (for instance, the cost associated with synthesis). One skilled in the art can easily make any necessary adjustments in accordance with the exigencies of the particular situation.

These methods described herein are by no means all-inclusive, and further methods to suit the specific application will be apparent to the ordinary skilled artisan. Moreover, the effective amount of the compositions can be further approximated through analogy to compounds known to exert the desired effect.

Therapeutic Inhibitor Compositions and Methods

In various embodiments, the present invention includes inhibitor compositions for inhibiting with the interaction between the mosquito salivary protein associated with a *Plasmodium* sporozoite and the *Plasmodium* sporozoite. In various embodiments, the inhibited mosquito salivary protein associated with a *Plasmodium* sporozoite is at least one of the group consisting of AGAP000607-PA (a salivary gland-1 like 3 protein; hereinafter "SG1L3"), AGAP001374-PA (hereinafter "TRIO"), AGAP009257-PA, AGAP009918-PA, AGAP010750-PA, AGAP001424-PA, AGAP001566-PA, AGAP007347-PA, AGAP008227-PA, AGAP008279-PA, AGAP008283-PA, AGAP011017-PA, AGAP011976-PA, AGAP012081-PA, AGAP013499-PA, AGAP002998-PA, AGAP003937-PA, AGAP004605-PA, AGAP011107-PA, AGAP013013-PA, AGAP009974-PA, AGAP000528-PA, and AGAP011026-PA, or variants thereof. Inhibition of the interaction between the mosquito salivary protein associated with a *Plasmodium* sporozoite and the *Plasmodium* sporozoite can be assessed using a wide variety of methods, including those disclosed herein, as well as methods known in the art or to be developed in the future.

One skilled in the art, based upon the disclosure provided herein, would understand that the inhibitor compositions and methods of the invention are useful in treating preventing and infection by a *Plasmodium* sporozoite.

The inhibitor compositions and methods of the invention that interfere with the interaction between the mosquito salivary protein associated with a *Plasmodium* sporozoite and the *Plasmodium* sporozoite include, but should not be construed as being limited to, a chemical compound, a protein, a peptide, a peptidomemetic, an antibody, a ribozyme, a small molecule chemical compound, a glycan, an antisense nucleic acid molecule (e.g., siRNA, miRNA, etc.), or combinations thereof. One of skill in the art would readily appreciate, based on the disclosure provided herein, that the inhibitor compositions of the invention include those that interfere with the interaction between the protein and the *Plasmodium* sporozoite. In some embodiments, the inhibitor compositions bind to the protein and interfere with the interaction between the protein and the *Plasmodium* sporozoite. In other embodiments, the inhibitor compositions bind to the *Plasmodium* sporozoite and interfere with the interaction between the protein and the *Plasmodium* sporozoite.

In various embodiments, the treatment of *Plasmodium* sporozoite infection in a subject is accomplished through passive antibody therapy (i.e., the transfer of antibodies to the *Plasmodium* sporozoite infected subject). In various embodiments, the inhibitor compositions and methods of the invention that interfere with the interaction between the mosquito salivary protein associated with a *Plasmodium* sporozoite and the *Plasmodium* sporozoite are used in combination with an antibiotic therapy. When used in combination, the antibiotic therapy can be administered before, during or after the administration of the inhibitor compositions of the invention.

Further, one of skill in the art would, when equipped with this disclosure and the methods exemplified herein, appreciate that an inhibitor composition includes such inhibitors as discovered in the future, as can be identified by well-known criteria in the art of pharmacology. Therefore, the present invention is not limited in any way to any particular inhibitor composition as exemplified or disclosed herein; rather, the invention encompasses those inhibitor compositions that would be understood by the routineer to be useful as are known in the art and as are discovered in the future.

Further methods of identifying and producing inhibitor compositions are well known to those of ordinary skill in the art, including, but not limited, obtaining an inhibitor from a naturally occurring source (i.e., *Streptomyces* sp., *Pseudomonas* sp., *Stylotella aurantium*). Alternatively, an inhibitor can be synthesized chemically. Further, the routineer would appreciate, based upon the teachings provided herein, that an inhibitor composition can be obtained from a recombinant organism. Compositions and methods for chemically synthesizing inhibitors and for obtaining them from natural sources are well known in the art and are described in the art.

Numerous vectors and other compositions and methods are well known for administering a protein or a nucleic acid construct encoding a protein to cells or tissues. Therefore, the invention includes a method of administering a protein or a nucleic acid encoding a protein that is an inhibitor. (Sambrook et al., 2012, Molecular Cloning: A Laboratory Manual, Cold Spring Harbor Laboratory, New York; Ausubel et al., 1997, Current Protocols in Molecular Biology, John Wiley & Sons, New York).

One of skill in the art will appreciate that inhibitors of the invention can be administered singly or in any combination. Further, inhibitors can be administered singly or in any combination in a temporal sense, in that they may be administered concurrently, or before, and/or after each other.

In various embodiments, any of the inhibitors of the invention described herein can be administered alone or in combination with other inhibitors of other molecules associated with *Plasmodium* sporozoite infection.

It will be appreciated by one of skill in the art, when armed with the present disclosure including the methods detailed herein, that the invention is not limited to treatment of a disease or disorder that is already established. Particularly, the disease or disorder need not have manifested to the point of detriment to the subject; indeed, the disease or disorder need not be detected in a subject before treatment is administered. That is, significant disease or disorder does not have to occur before the present invention may provide benefit. Therefore, the present invention includes a method for preventing infection in a subject, in that an inhibitor composition, as discussed previously elsewhere herein, can be administered to a subject prior to the onset of the infection.

The invention encompasses administration of an inhibitor to practice the methods of the invention; the skilled artisan would understand, based on the disclosure provided herein, how to formulate and administer the appropriate inhibitor to a subject. Indeed, the successful administration of the inhibitor has been reduced to practice herein. However, the present invention is not limited to any particular method of administration or treatment regimen.

Pharmaceutical Compositions

The present invention includes the treatment of a *Plasmodium* sporozoite infection in a subject by the administration of a therapeutic composition of the invention to a subject in need thereof. In one embodiment, the therapeutic composition of the invention is an inhibitor composition. In one embodiment, the therapeutic composition of the invention for the treatment of *Plasmodium* sporozoite infection is at least one antibody that specifically binds to at least one mosquito salivary protein associated with a *Plasmodium* sporozoite. In various embodiments, the therapeutic composition comprises at least one antibody that specifically binds to at least one of the group consisting of AGAP000607-PA (a salivary gland-1 like 3 protein; hereinafter "SG1L3"), AGAP001374-PA (hereinafter "TRIO"), AGAP009257-PA, AGAP009918-PA, AGAP010750-PA, AGAP001424-PA, AGAP001566-PA, AGAP007347-PA, AGAP008227-PA, AGAP008279-PA, AGAP008283-PA, AGAP011017-PA, AGAP011976-PA, AGAP012081-PA, AGAP013499-PA, AGAP002998-PA, AGAP003937-PA, AGAP004605-PA, AGAP011107-PA, AGAP013013-PA, AGAP009974-PA, AGAP000528-PA, and AGAP011026-PA, or variants thereof In various embodiments, the treatment of *Plasmodium* sporozoite infection in a subject is accomplished through passive antibody therapy (i.e., the transfer of antibodies to the *Plasmodium* sporozoite infected subject).

Administration of the therapeutic composition in accordance with the present invention may be continuous or intermittent, depending, for example, upon the recipient's physiological condition, whether the purpose of the administration is therapeutic or prophylactic, and other factors known to skilled practitioners. The administration of the compositions of the invention may be essentially continuous over a preselected period of time or may be in a series of spaced doses. Both local and systemic administration is contemplated. The amount administered will vary depending on various factors including, but not limited to, the composition chosen, the particular disease, the weight, the physical condition, and the age of the subject, and whether prevention or treatment is to be achieved. Such factors can be readily determined by the clinician employing animal models or other test systems which are well known to the art.

When the compositions of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the compositions of the invention can be prepared by procedures known in the art using well known and readily available ingredients. The compositions of the invention can also be formulated as solutions appropriate for parenteral administration, for instance by intramuscular, subcutaneous or intravenous routes.

Thus, the composition may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

In general, water, suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

These methods described herein are by no means all-inclusive, and further methods to suit the specific application will be apparent to the ordinary skilled artisan. Moreover, the effective amount of the compositions can be further approximated through analogy to compounds known to exert the desired effect.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1

Mosquito Saliva Protein SG1L3 as a Novel Malaria Vaccine Target

Figure 1A:
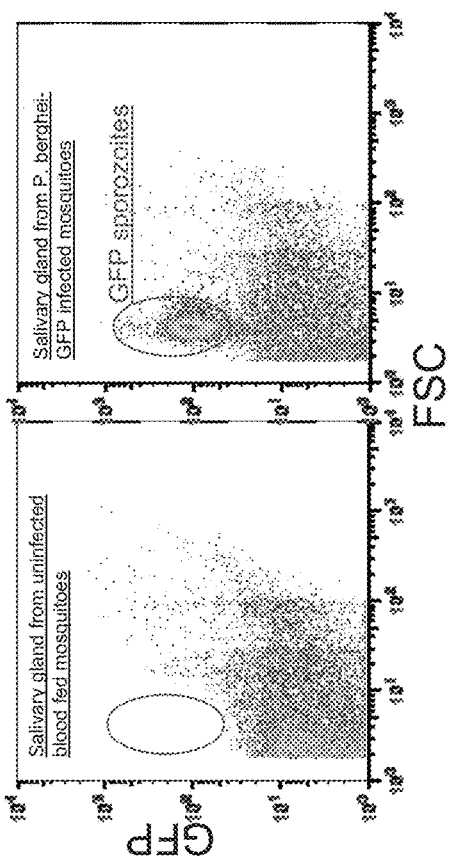
Figure 1B:
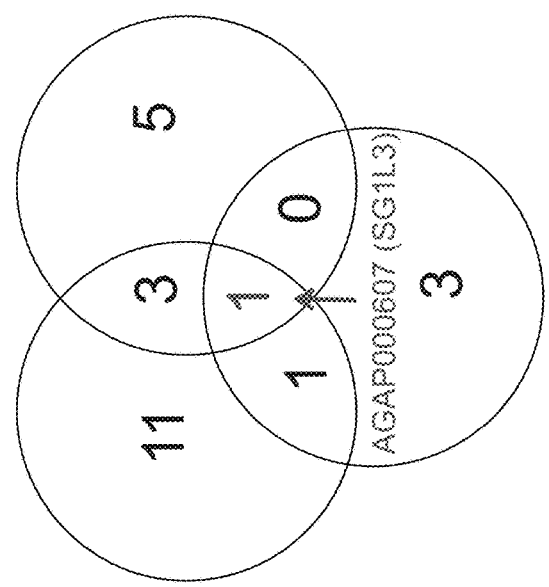

The results described herein demonstrate that mosquito saliva proteins associated with a *Plasmodium* sporozoite are novel vaccine targets for immunization against malaria.
Identification of *Anopheles* Proteins that Interact with *Plasmodium* Sporozoites To identify mosquito saliva proteins that are associated with a *Plasmodium* sporozoite, fluorescence-activated cell sorting (FACS) was used to isolate and purify GFP-expressing *P. berghei* sporozoites from *A. gambiae* salivary glands (FIG. 1A). NanoLC/MS-MS analysis was performed to categorize mosquito proteins that were co-purified with *Plasmodium* sporozoites. Three separate experiments identified a total of 24 *A. gambiae* proteins that could potentially be associated with the sporozoites (FIG. 1B, FIG. 6). One protein (AGAP000607, SG1L3) was identified in all 3 independent studies, and was therefore selected for in-depth characterization.

To validate whether SG1L3 was associated with *Plasmodium* sporozoites, the sporozoites purified from salivary glands (SG) and midguts (MG) were stained. Rabbit antibody against SG1L3 could detect a signal from mosquito SG sporozoites but not those from MG (FIG. 1C).

Figure 2B:
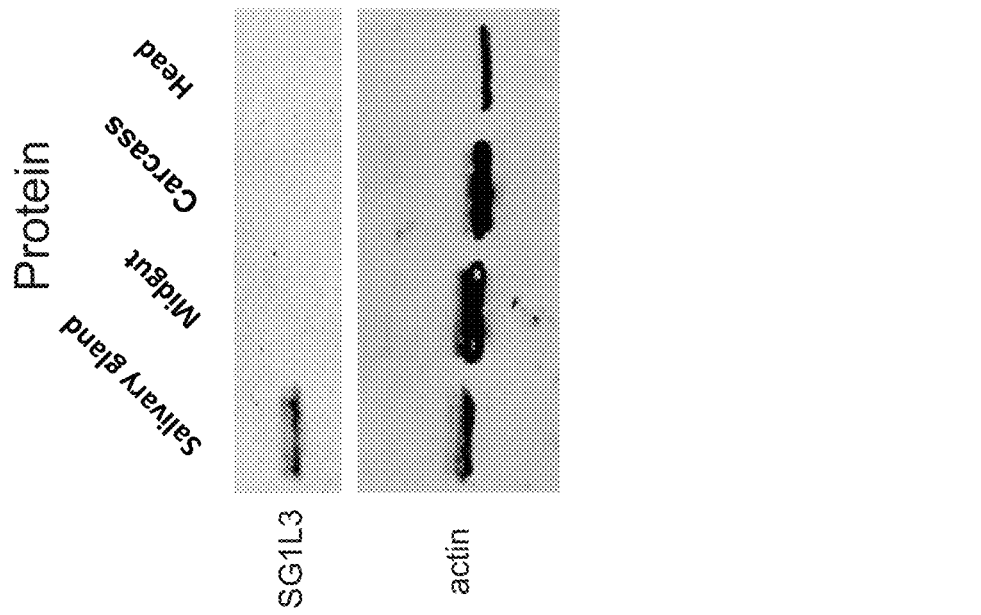
FIG. 2A through FIG. 2D depict the results of SG1L3 expression analyses in *A. gambiae* salivary glands.
Figure 2A:
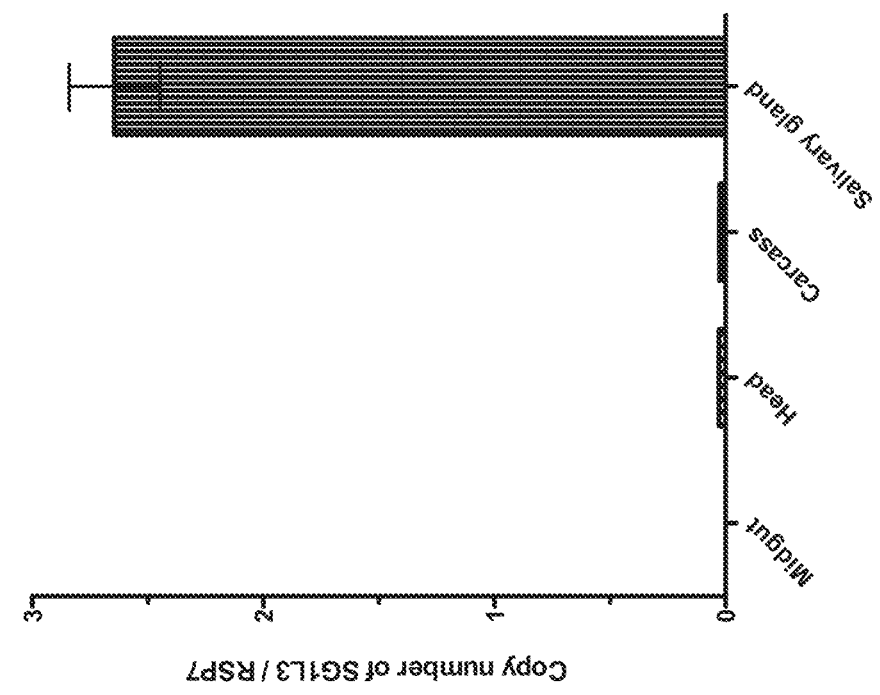
Figure 2D:
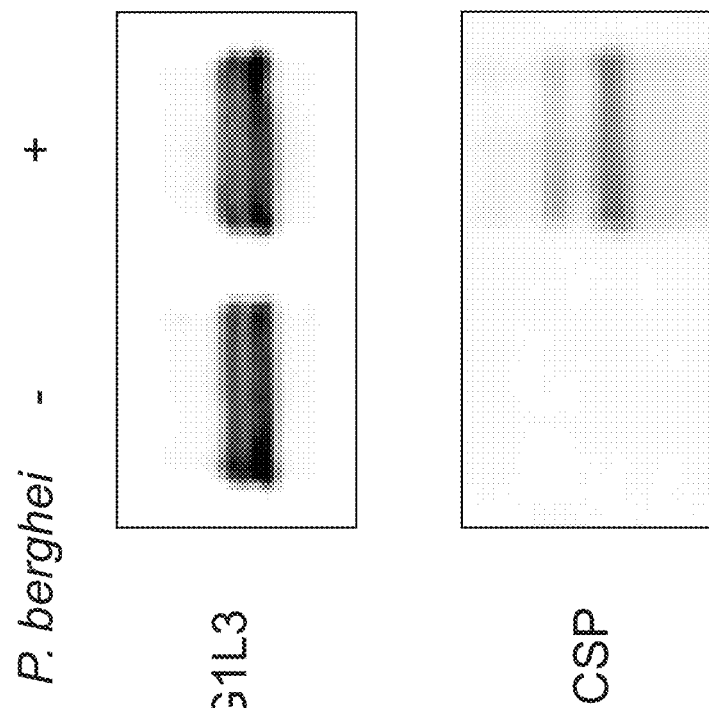
Figure 2C:
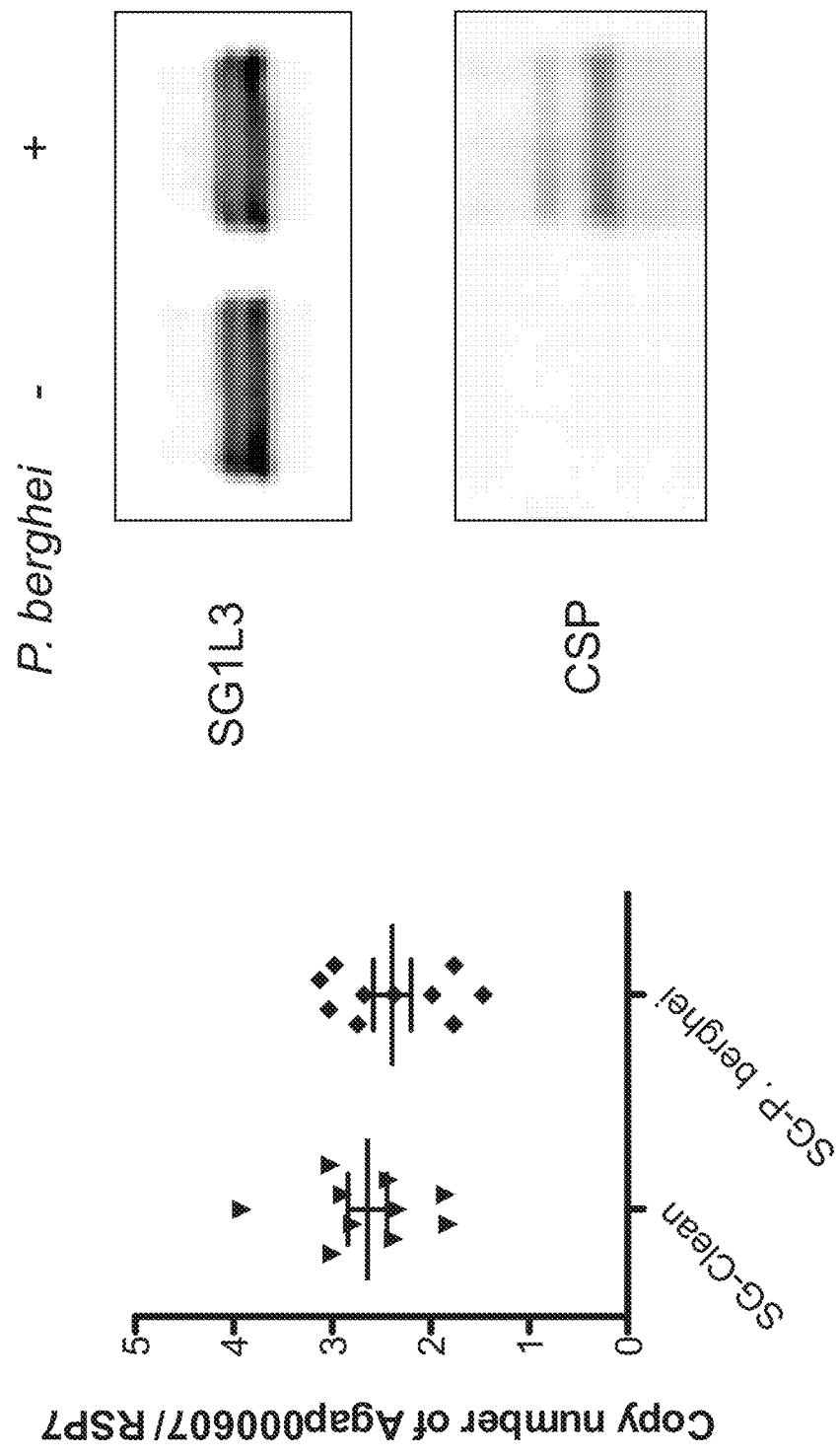

SG1L3 was only expressed in *A. gambiae* salivary glands (FIG. 2A, FIG. 2B). The invasion of *Plasmodium* sporozoites into the salivary glands does not alter the expression of SG1L3, both at the mRNA and protein levels (FIG. 2C, FIG. 2D).

SG1L3 Antibodies Interfere with Sporozoites Transmission

Figure 3A:
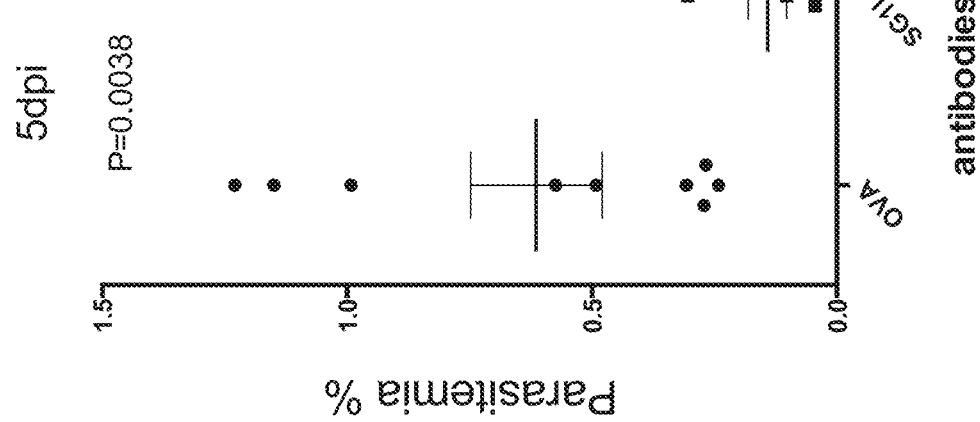
FIG. 3A through FIG. 3D depict the results of experiments demonstrating the effects of immunizing mice with SG1L3 antibodies.
Figure 3B:
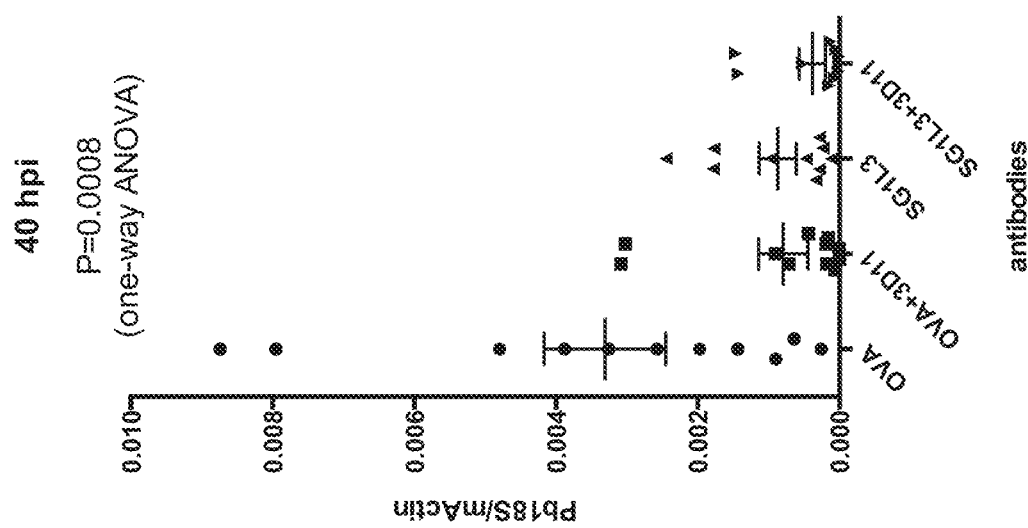

It was assessed whether passive immunization with SG1L3 antibodies could interfere with *Plasmodium* sporozoites transmission from mosquito to the mammalian host. Rabbit IgG against SG1L3 were transferred to naïve mice, and these mice were challenged with *P. berghei*-infected *A. gambiae* mosquitoes. A lower *Plasmodium* liver burden was observed in SG1L3 antibody receiving animals (FIG. 3A), suggesting that fewer sporozoites had reached the liver and invaded the hepatocytes. Furthermore, these animals had lower parasitemia levels at the early stage of the disease (FIG. 3B). In addition, when combined with 3D11 mAb against *P. berghei* CSP, a known reagent that inhibits the *Plasmodium* sporozoite transmission, antibodies against SG1L3 further reduced the *Plasmodium* liver burden (FIG. 3A). These results demonstrate that antibodies to *Plasmodium* antigen CSP and mosquito saliva protein have a synergetic effect.

Figures 3C, 3D:
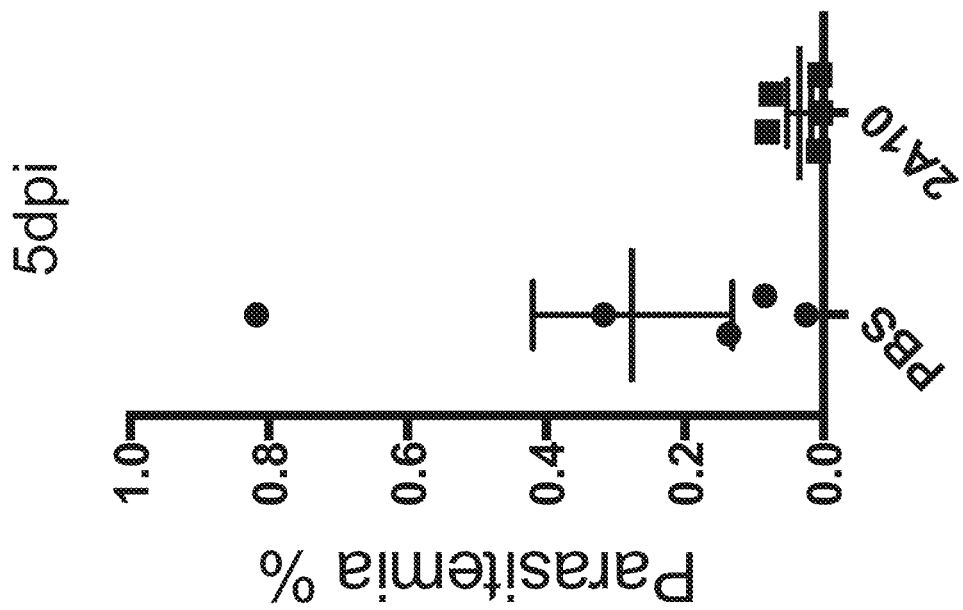

Monoclonal antibodies to SG1L3 were then generated. When transferred to the mice, mAb (2A10) appeared able to not only reduce the *Plasmodium* burden (FIG. 3C), but also to protect 3 out of 5 mice from infection (FIG. 3D).

Figure 4A:
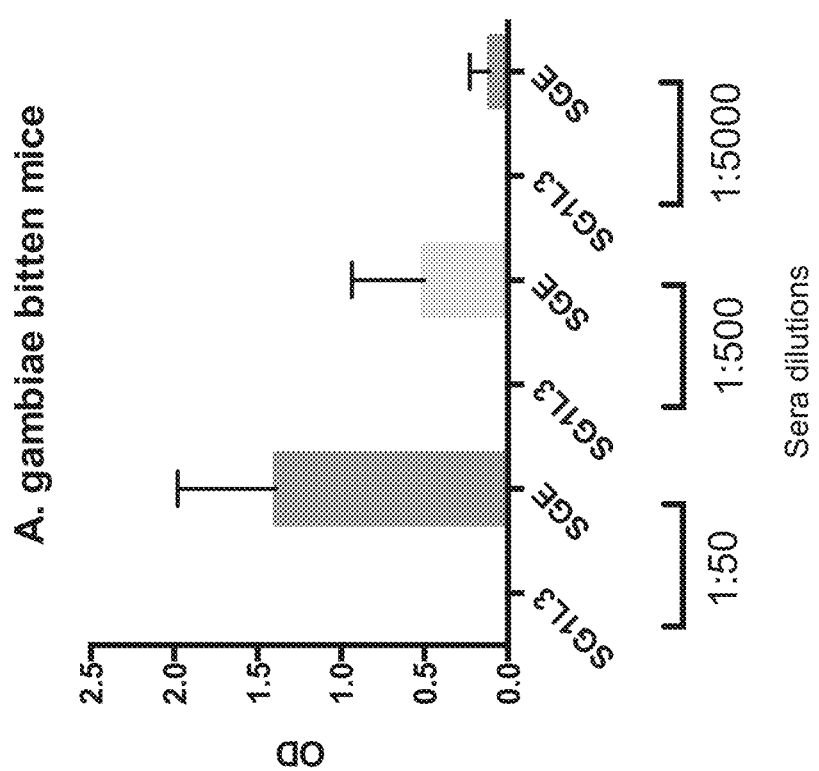
FIG. 4A through FIG. 4B depict the antibody response by mice in response to being bitten by *A. gambiae*.
Figure 4B:
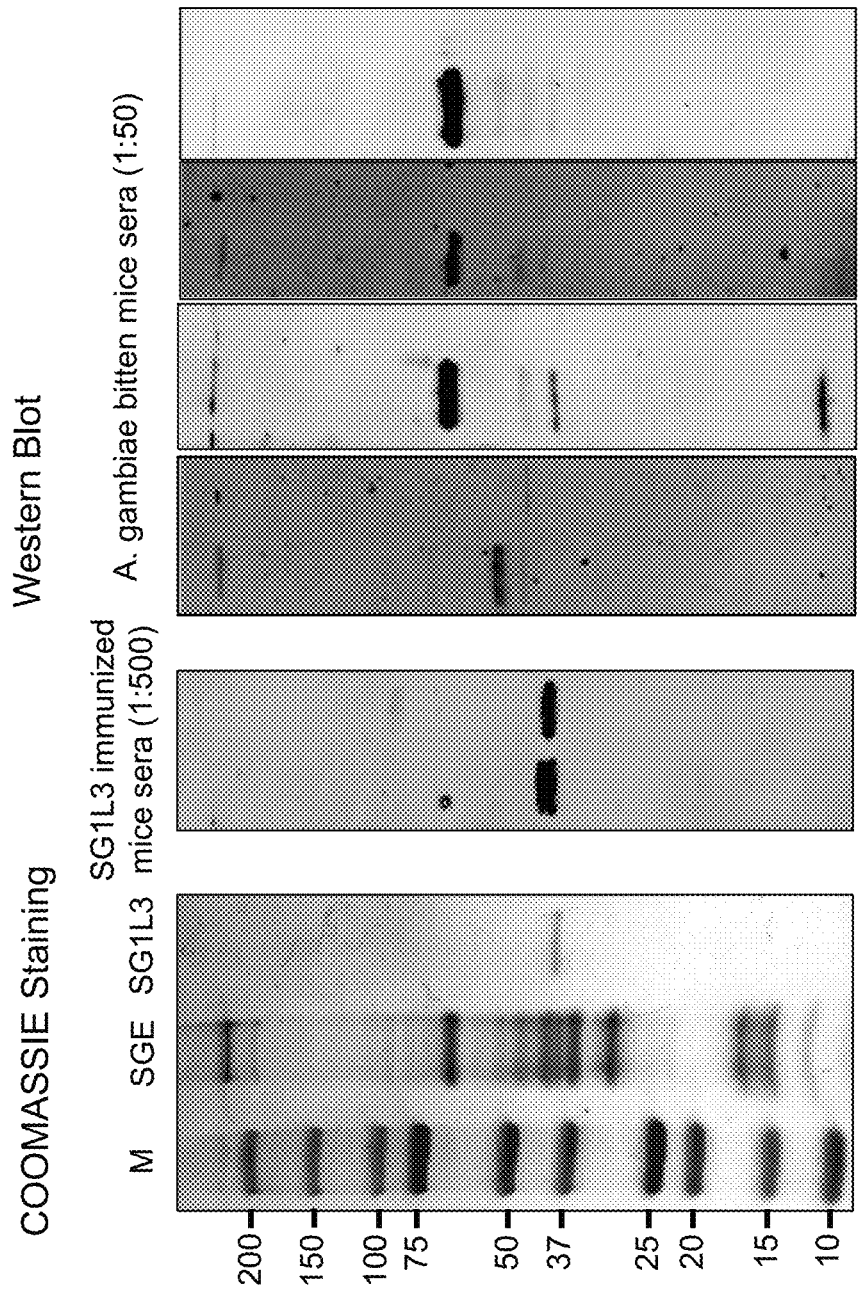

Vertebrate Hosts Generate Minimal Amount of IgG Antibodies to SG1L3 by Mosquito Bites SG1L3 is a component of mosquito saliva and is injected into mammalian hosts during blood feeding. It was thus investigated whether mosquito bites could elicit antibody responses to SG1L3. The sera from mice that were repeatedly bitten by *A. gambiae* mosquitoes were tested. ELISA and Western blot results showed that, though mice could generate strong reactions to whole mosquito salivary gland extracts, the antibodies to SG1L3 were barely detectable (FIG. 4A). The major immunogens from mosquito saliva were proteins with sizes of 300 KDa, 65 KDa, and 15 KDa (FIG. 4B), which may correspond to gSG5, 5'-nucleotidase, and gSG6, as previously reported.

SG1L3 Facilitates *Plasmodium* Sporozoite Traversal Through Host Cells

Figure 5:
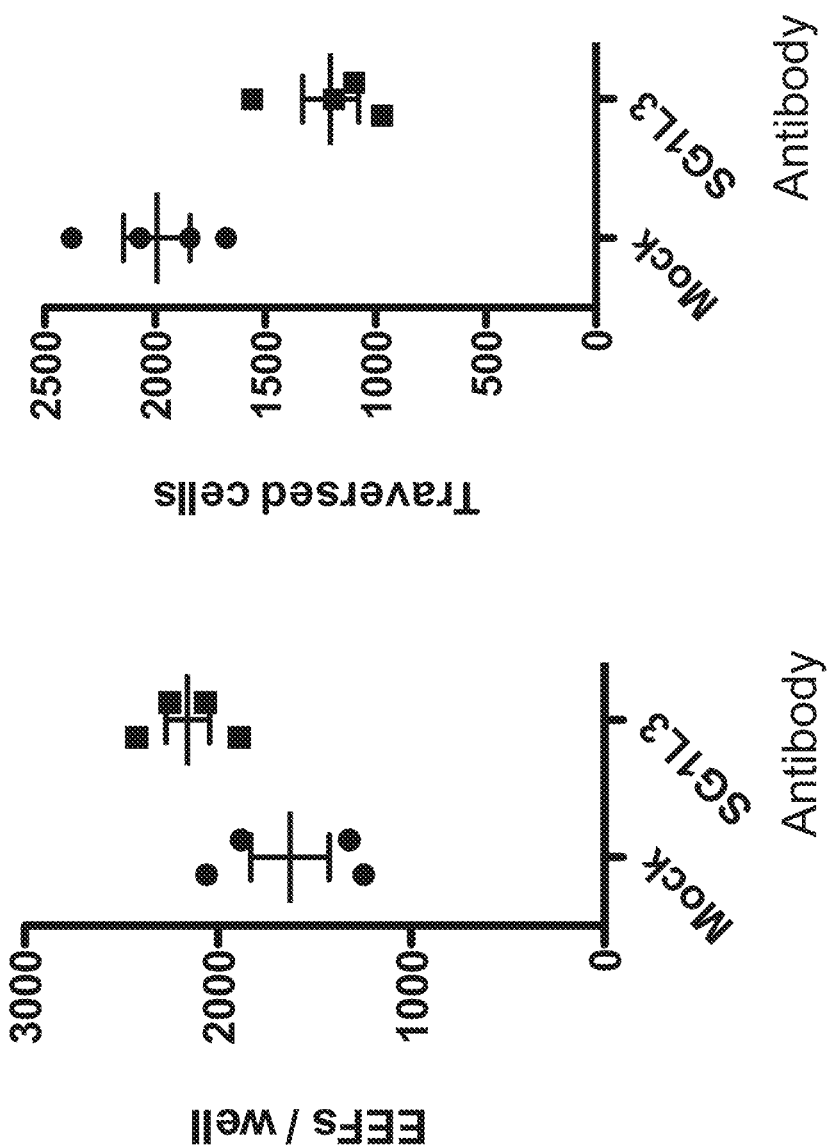
FIG. 5 depicts the effect of SG1L3 antibody on *Plasmodium* sporozoite invasion (measured by quantity of exo-erythrocytic forms) and traverse into host cells.

It was observed that the antibody to SG1L3 interfered with *Plasmodium* sporozoite transmission in vivo. It was next assessed whether SG1L3 antibody inhibited sporozoite traversal or invasion of host cells. FIG. 5 shows that the SG1L3 antibody does not prevent the sporozoites invasion into hepatoma cells, even at the highest concentration tested (5 mg/mL). However, when cells were incubated with SG1L3 antibody, the number of cells traversed by sporozoites (measured by influx of fluorescent Dextran) was significantly reduced (FIG. 5). These results are consistent with the explanation that the SG1L3 binding to sporozoites facilitates the cell traversal by sporozoites, which is required for sporozoites to reach the hepatocytes in vivo.

Example 2

Mosquito Saliva Protein SG1L3 is an Effective Novel Malaria Vaccine Target

The data described herein demonstrate that mosquito saliva proteins associated with a *Plasmodium* sporozoite are effective as novel vaccine targets for immunization against malaria as compared to an ovalbumin (OVA) control.

Immunization

Recombinant SG1L3 or OVA were emulsified in Complete Freund's Adjuvant (CFA) and administered subcutaneously to mice (10 μg protein per mouse). Two subsequent immunizations were emulsified in Incomplete Freund's Adjuvant (IFA). Emulsions were administered at 200 mL per mouse, 3 times at two week intervals.

*Plasmodium* Challenge

Figure 7:
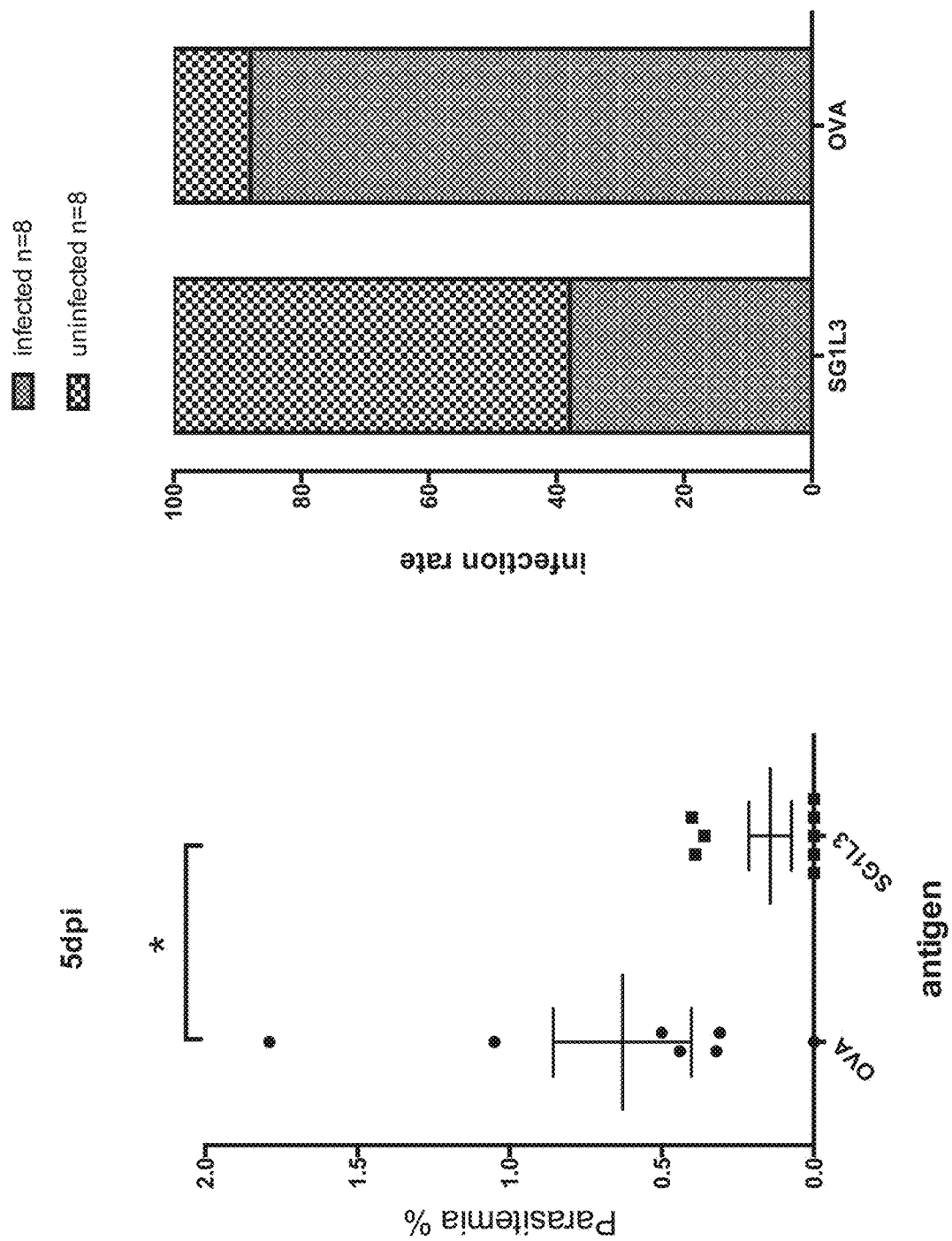
FIG. 7 depicts the results of experiments demonstrating that subcutaneous treatment of SG1L3 antibodies in mice is effective at reducing the infection rate of *Plasmodium* sporozoite as compared to an ovalbumin (OVA) control.

Infected mosquitoes were selected based on GFP signals expressed by parasites in their thorax, then randomly aliquoted into individual coffee cups with mesh covers. The infectious mosquito bite challenges were performed at the following day with two infectious bites per mouse. The blood parasite burdens were quantified by daily measurement of parasitemia starting from 4 days post infection. Results are shown in FIG. 7.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An immunogenic composition comprising the 3D11 monoclonal antibody that specifically binds to *Plasmodium berghei* circumsporozoite protein (CSP), and a wild-type sequence of the full-length salivary gland-1 like 3 protein (SG1L3) isolated from the salivary glands of *Anopheles gambiae* mosquito, wherein the SG1L3 has the designation AGAP000607-PA.

2. A method of inducing an immune response to the SG1L3 protein in a mammalian subject, the method comprising administering to the subject an effective amount of the immunogenic composition of claim 1.

3. The method of claim 2, wherein the subject is currently infected with *Plasmodium* sporozoites.

4. The method of claim 2, wherein the subject is not currently infected with *Plasmodium* sporozoites.

* * * * *